United States Patent
Karp et al.

(10) Patent No.: US 10,859,563 B2
(45) Date of Patent: Dec. 8, 2020

(54) ERYTHROCYTE AGGREGATION AND LEUKOCYTE ISOLATION

(71) Applicant: GENERAL ELECTRIC COMPANY, Schenectady, NY (US)

(72) Inventors: Jessica Godin Karp, Schenectady, NY (US); Xiaohui Chen, Schenectady, NY (US); Kashan Ali Shaikh, Clifton Park, NY (US); Mengli Wang, Rexford, NY (US); Ralf Lenigk, Schenectady, NY (US); Christine Lynne Surrette, Albany, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 175 days.

(21) Appl. No.: 14/956,067

(22) Filed: Dec. 1, 2015

(65) Prior Publication Data
US 2017/0153223 A1 Jun. 1, 2017

(51) Int. Cl.
*G01N 33/50* (2006.01)
*G01N 33/49* (2006.01)
(Continued)

(52) U.S. Cl.
CPC .... *G01N 33/5002* (2013.01); *B01L 3/502715* (2013.01); *B01L 3/502738* (2013.01);
(Continued)

(58) Field of Classification Search
USPC ......... 422/407, 502–504, 551, 554, 600–603
See application file for complete search history.

(56) References Cited

U.S. PATENT DOCUMENTS

| | | | |
|---|---|---|---|
| 5,993,750 A * | 11/1999 | Ghosh | B01F 5/0604 165/185 |
| 6,197,575 B1 * | 3/2001 | Griffith | B01J 19/0046 435/288.4 |

(Continued)

FOREIGN PATENT DOCUMENTS

| | | |
|---|---|---|
| JP | 2005509882 A | 4/2005 |
| WO | 2003044481 A3 | 5/2006 |

(Continued)

OTHER PUBLICATIONS

Microplate Standards, ANSI SLAS Apr. 2004 (R2012): Well Positions (https://www.slas.org/resources/information/industry-standards/) (Year: 2011).*

(Continued)

*Primary Examiner* — Dean Kwak
(74) *Attorney, Agent, or Firm* — Fletcher Yoder, P.C.

(57) ABSTRACT

A device and/or methodology are described that include a mechanism for separating erythrocytes from other constituents of blood and for purifying leukocytes from blood. The separation and purification aspects may be provided in separate components or within the same component. The separation aspect assists in separating erythrocytes (red blood cells) from other cells in blood, such as by aggregation of the red blood cells. A suitable aggregation device or device component uses chambers with at least one small dimension (e.g., a microfluidic chip) to control the interaction of the blood with a solution containing a high molecular weight polymer (e.g., dextran) to achieve separation.

8 Claims, 11 Drawing Sheets

(51) Int. Cl.
  *B01L 3/00* (2006.01)
  *C12Q 1/24* (2006.01)
  *G01N 1/40* (2006.01)

(52) U.S. Cl.
  CPC ... *B01L 3/502761* (2013.01); *B01L 3/502769* (2013.01); *C12Q 1/24* (2013.01); *G01N 33/491* (2013.01); *B01D 2313/18* (2013.01); *B01D 2313/50* (2013.01); *B01L 2200/0647* (2013.01); *B01L 2300/16* (2013.01); *G01N 2001/4088* (2013.01)

(56) References Cited

U.S. PATENT DOCUMENTS

| | | | |
|---|---|---|---|
| 7,166,443 B2 | 1/2007 | Walker et al. | |
| 7,307,150 B2 | 12/2007 | Tsai et al. | |
| 8,318,439 B2 | 11/2012 | Battrell et al. | |
| 9,347,440 B2* | 5/2016 | Lebl | B01L 3/50273 |
| 9,678,079 B2* | 6/2017 | Godec | B01L 3/5027 |
| 2003/0113925 A1* | 6/2003 | Gordon | G01N 15/1475 506/3 |
| 2003/0129665 A1 | 7/2003 | Selvan et al. | |
| 2003/0175947 A1* | 9/2003 | Liu | B01F 11/0071 435/288.5 |
| 2005/0142570 A1 | 6/2005 | Parthasarathy et al. | |
| 2006/0051250 A1* | 3/2006 | Gonzalez | B01L 3/0268 422/400 |
| 2007/0248984 A1 | 10/2007 | Collins | |
| 2008/0219890 A1* | 9/2008 | Lawson | B01L 3/502715 422/81 |
| 2008/0242553 A1* | 10/2008 | Kayyem | B01L 3/5027 506/9 |
| 2013/0082012 A1 | 4/2013 | Lean et al. | |
| 2014/0302483 A1 | 10/2014 | Kauling et al. | |

FOREIGN PATENT DOCUMENTS

| | | |
|---|---|---|
| WO | 03/031938 A2 | 4/2013 |
| WO | 2014145075 A2 | 9/2014 |
| WO | 2014/170662 A1 | 10/2014 |

OTHER PUBLICATIONS

European Search Report and Opinion issued in connection with corresponding EP Application No. 16200924.5 dated Mar. 24, 2017.

Pribush, A., et al.; "The mechanism of the dextran-induced red blood cell aggregation", European Biophysics Journal, pp. 85-94, vol. 36, Issue 2, Feb. 2007.

Neu, Bjorn, et al.; "Effects of Dextran Molecular Weight on Red Blood Cell Aggregation", Biophysical Journal, pp. 3059-3065, vol. 95, Issue 6, Sep. 15, 2008.

Hou, H.W., et al., "Microfluidic Devices for Blood Fractionation," Micromachines, vol. 2, No. 4, pp. 319-343 (2011).

Soohoo, J.R., and Walker, G.M., "Microfluidic aqueous two phase system for leukocyte concentration from whole blood," Biomedical Microdevices, vol. 11, No. 2, pp. 323-329 (2009).

* cited by examiner

INDIVIDUAL RBCs

RBC AGGREGATES

US 10,859,563 B2

ERYTHROCYTE AGGREGATION AND LEUKOCYTE ISOLATION

STATEMENT REGARDING FEDERALLY SPONSORED RESEARCH & DEVELOPMENT

This invention was made with Government support under contract number HDTRA1-12-C-0098 awarded by DTRA. The Government has certain rights in the invention.

BACKGROUND

The subject matter disclosed herein relates to erythrocyte aggregation and leukocyte isolation.

In various research and medical contexts, it may be desirable to separate or isolate certain components of an initial composition into one or more purified and/or separated constituents. By way of example, whole blood is a complex composition having various molecular and cellular constituents. In various contexts, it may be desirable to isolate or separate one or more of the whole blood constituents, such as for research purposes, for diagnostic purposes, or as a precursor or step in a medical treatment or preparation of a medically useful composition. The most common way to separate blood components involves the use of a density gradient media and a centrifuge to achieve high efficiency separation. Other common methods include red blood cell (RBC) lysis and red blood cell aggregation in a dextran solution, but separation performance is not as good.

For example, it may be desirable to separate or purify leukocytes (i.e., white blood cells or WBCs) from a whole blood sample. Several large volume approaches to leukocyte purification exist. Ficoll-Paque density separation is one such technique, but requires laboratory equipment (a centrifuge), a skilled operator to identify and remove the desired cell layer, and has a lower limit on blood volume due to the increasing difficulty in locating and removing the cell layer as it shrinks in size. Erythrocyte lysis is another approach for leukocyte purification. This technique also requires a centrifuge (and therefore, a laboratory) for re-concentration of the diluted cells, and it can damage the leukocytes as well.

Microfluidic approaches also exist. Deterministic lateral displacement is one such technique, in which the different deformability and size characteristics of white and red blood cells is exploited as the cells pass through an array of small pillars. In such devices, the pillar size and spacing must be small (~20-40 µm) and well controlled, making reliable fabrication of these devices a costly endeavor. In addition, since separation is based in part on size, a purity tradeoff will exist for small leukocytes that are similar in size to erythrocytes (i.e., red blood cells). Cross-flow separations use small side channels for erythrocyte removal by size and/or deformation, but also require small device dimensions that bring associated cost and reliability concerns (such as potential for device clogging). Hydrodynamic techniques also exist, but generally these are high-flow approaches that may not perform well for a small volume sample (e.g., less than or equal to 100 µl), and often involve sample dilution or high flow velocities that may damage cells.

Thus, a need exists for leukocyte separation and/or purification approaches that do not require bulky laboratory equipment (e.g., a centrifuge) and which provide high purity with small input volumes (i.e., small samples) and with low absolute cell loss.

BRIEF DESCRIPTION

In a first aspect, a method for separating blood components is provided. In accordance with this approach, a blood sample is loaded into a microfluidic chamber in which a solution of high-molecular weight polysaccharide is present. The blood sample has higher density than the solution. The dimensions of the microfluidic chamber enable stabilization of the higher density blood sample above the lower-density solution despite being energetically unstable. Red blood cells present in the blood sample are aggregated at the interface formed between the solution and the blood sample. The red blood cells, when aggregated, sediment into the solution and out of the blood sample leaving a red blood cell separated sample.

In a further aspect, a blood component separation device is provided. The device includes: a loading port configured to receive a blood sample; an aggregation chamber configured to receive the blood sample when loaded in the loading port and to hold a solution of a high-molecular weight polysaccharide, wherein the aggregation chamber is sized in an at least one dimension to generate a surface tension between the blood sample and the solution, when present, sufficient to stabilize the blood sample over the solution within the aggregation chamber, wherein the blood sample is higher density than the solution; and an outlet of the aggregation chamber configured to output a red blood cell separated sample.

In another aspect, a microfluidic device is provided. The device includes: one or more loading wells; for each loading well, at least one respective red blood cell aggregation channel, wherein each aggregation channel has at least one dimension less than or equal to 450 µm; at least one respective white blood cell capture channel configured to receive an output from one or more of the red blood cell aggregation channels and configured to differentially bind at least one white blood cell type in the output.

In an additional aspect, a microfluidic device is provided. The device includes: one or more loading wells; for each loading well, at least one respective red blood cell aggregation channel, wherein each aggregation channel has at least one dimension less than or equal to 450 µm and wherein each red blood cell aggregation channel comprises an antibody coated surface configured to bind at least one white blood cell type of interest.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
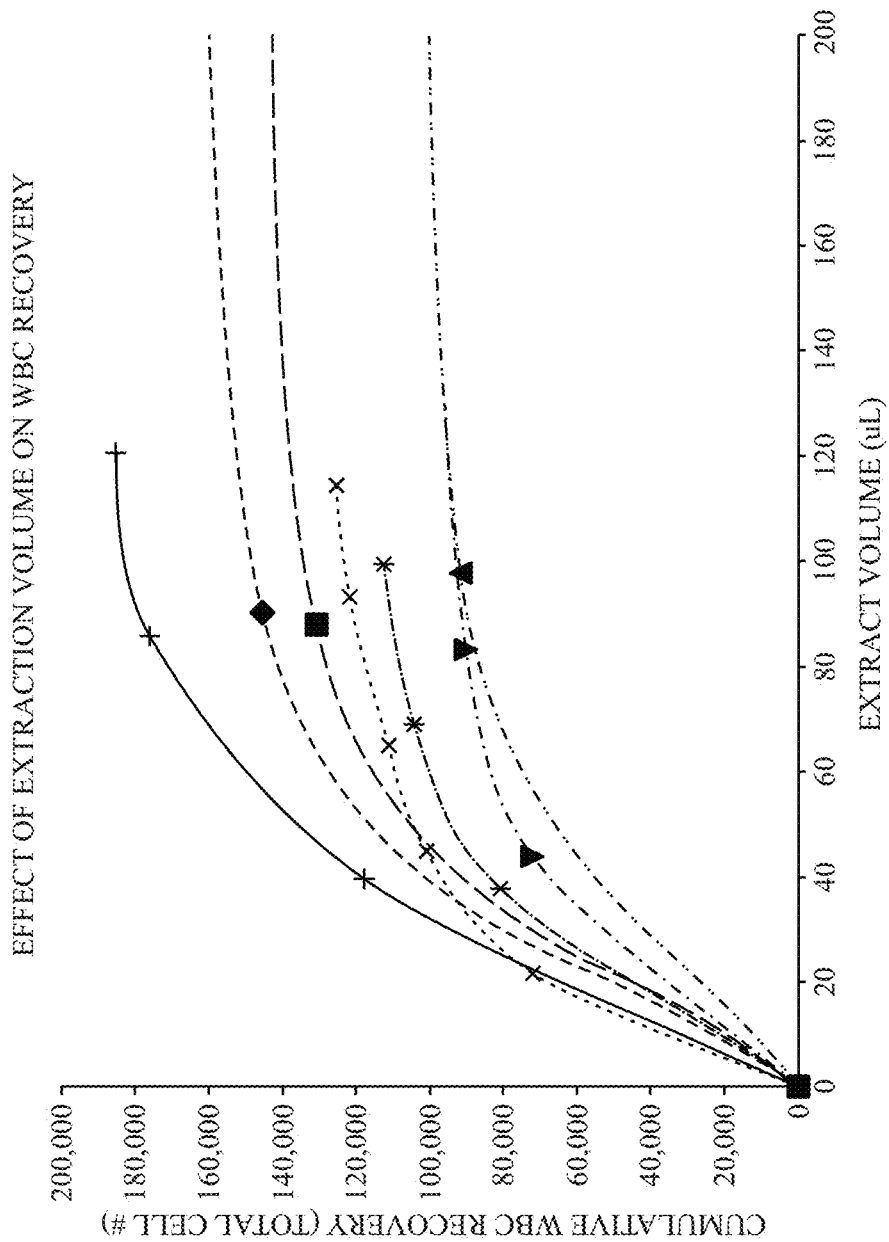
FIG. 1 depicts effects of extraction volume on white blood cell recovery, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

When blood is mixed with certain polymers, such as high-molecular weight dextran, red blood cells (i.e., erythrocytes) will aggregate and sediment out of solution, allowing for the separation of red blood cells from other constituents of blood. In accordance with the present approaches, microfluidic chambers are used to control the interaction between a blood sample (either whole, diluted, or concentrated blood) and a polymer-containing solution. Blood has a density of ~1.06 g/dl, while dextran solution densities vary depending on their composition, though dextran solutions are less dense than blood at the concentrations typically used for red blood cell sedimentation.

At the macro-scale, if one attempts to manually layer blood over a dextran solution, the blood tends to stream to the bottom with limited interaction between the two fluids, thus failing to aggregate and sediment out the red blood cells to a meaningful extent. At the macro scale, this deficiency may be partially addressed by mixing of the fluids so as to achieve uniform red blood cell aggregation.

Conversely, in accordance with the present approach, microfluidic chambers are used that provide controlled layering of whole blood over a dextran solution (or other solution of a high-molecular weight polymer), resulting in significant interaction between the two fluids without mixing. The blood and dextran interact at the interface of the fluids, leading to the formation of red blood cell aggregates at the interface. These aggregates then sediment into the dextran solution due to gravity. This process continues, resulting in the sedimentation of the majority of aggregated red blood cells at the bottom of the device, while the majority of white blood cells (i.e., leukocytes) and other blood components remain in the supernatant. In accordance with these principles, red blood cells may be aggregated from the sample, allowing separation of the majority of red blood cells from the white blood cells and other blood components. The extracted red blood cell separated fluid can be further processed to purify and isolate the white blood cells for analysis, as also discussed herein.

In accordance with the present approaches, this method of layering blood over dextran allows for rapid (e.g., 10, 15, or 20 minutes), high-purity (e.g. 95% to 99% erythrocyte depletion) separation of leukocytes from whole blood, especially from a small volume of blood (e.g., less than or equal to 100 μl whole blood). The present approach is both low-shear and label-free, for minimal activation/modification of the leukocyte sample. This method may also have applications in plasma or platelet separations. Conversely, it is possible that this approach could be used for erythrocyte separation as well, such as by harvesting and releasing the aggregated erythrocytes. Of particular note for certain applications, the present approach is noteworthy in its ability take a small volume heterogeneous (e.g., 1000:1) sample and to deliver a separated sample that is high purity (e.g., drastically reduced erythrocyte count) which can be processed over an affinity surface to capture leukocytes so as to obtain a high yield (e.g., high percentage leukocytes recovered) and high density (leukocytes close together on surface).

Red Blood Cell Aggregation: Principles of operation—As discussed herein, the red blood cell depletion efficiency in the described microfluidic device is a function of the interplay between surface tension (typically a function of channel geometry), instability of the blood/dextran interface (i.e., Rayleigh-Taylor instability), and the dextran aggregation properties (dextran concentration and molecular weight). Though dextran is described in these examples and throughout as being the aggregation medium, it should be appreciated that dextran is provided merely as one example of a suitable solution, and that other high molecular weight polymers may be used instead of or in addition to dextran to induce red blood cell aggregation. The chamber height is one factor, with a channel height of 450 μm exhibiting rapid blood streaming (density-mediated descent of whole blood), while a channel height of 225 μm exhibits much more aggregation-mediated sedimentation of red blood cells (leaving the majority of white blood cells in the upper portion of the device for later recovery). The density of the dextran solution can also be tuned or modified to adjust performance of a microfluidic based separation device, such as to improve the extraction efficiency of white blood cells. Other factors, such as temperature, that play a role in typical aggregation kinetics may also be tuned or adjusted to affect the performance of such a separation device.

Prior to discussing particular implementations and device examples, general principles of operation for presently contemplated blood component separation devices will be briefly discussed. One principle related to the operation of a present separation device is Rayleigh-Taylor (RT) instability, which is present when a more dense fluid is layered over a less-dense fluid. This is an energetically unfavorable condition, and small perturbations to the interface will tend to evolve into an instability through which the upper fluid can stream down into the lower fluid, while the lower fluid rises to displace the upper fluid. The result is the restoration of the system to an energetically favorable condition (i.e., less-dense fluid atop the more-dense fluid). On a large scale (where surface tension is negligible), the rate at which such instabilities evolve is mainly dictated by the magnitude of the density mismatch between the two fluids (smaller density mismatch means a more stable interface). On a smaller scale, surface tension can play a role in stabilizing the interface, thus allowing the otherwise energetically unfavorable condition to be maintained.

In the present blood component separation context, the time scale of the dextran aggregation is relatively fixed, while the time scale of the Rayleigh-Taylor instability evolution can be manipulated by design of the interface structures, e.g., the dimensions of the microfluidic chambers or channels. With a rapidly-evolving Rayleigh-Taylor instability, the entire blood (all contents) will sink and the dextran will rise. With a more slowly evolving instability, such as slowed due to the surface tension dynamics imposed by the microfluidic interface, the effects of dextran aggregation are more pronounced. In the slower case, red blood cells aggregate and sediment into the dextran solution, leaving the rest of the blood contents (e.g., plasma, platelets, and white blood cells) behind. As more and more red blood cells separate from the blood, the density mismatch changes since dextran and the resulting plasma have a similar density (see Table 1, below). Sedimentation of individual platelets and white blood cells in plasma is relatively slow, so the white blood cell purification and recovery can be quite high as long as white blood cells are not trapped by red blood cell aggregates as they sediment, which can itself be a function of the speed with at which the red blood cells aggregate, with faster aggregation times resulting in more white blood cell trapping. Thus, by slowing the evolution of the Rayleigh-Taylor instability, the dextran-mediated red blood cell aggregation dominates, removing the red blood cells from the plasma while leaving most of the remaining cells localized to the original volume occupied by the blood sample, where they can be recovered.

TABLE 1

Density of various components of blood and dextran

| | Density (g/mL) |
|---|---|
| Whole blood | 1.055-1.065 |
| White Blood Cells | 1.06-1.08 |
| Platelets | 1.06 |
| 3% dextran | 1.02 |
| Blood plasma | 1.02 |

In addition to surface tension (which can be controlled by design and sizing of the interface structures), the evolution of the Rayleigh-Taylor instability can be controlled by adjusting the density of the dextran solution relative to the whole blood density (such as via addition of one or more density adjusting additives). In such a context, increasing the density of the dextran solution to slow the evolution of the Rayleigh-Taylor instability may be balanced against any increase in viscosity that would slow the sedimentation rate of the red blood cell aggregates.

With respect to the aggregation properties of various dextran solutions, suitable solutions may have 1% to 10% dextran concentration at a molecular weight of 100-1,500 kDa. Aggregability peaks at around a 3% dextran concentration at a molecular weight of 500-1,000 kDa, and drops off with increasing or decreasing concentration or molecular weight. A variety of other factors, such as plasma protein content, cell age, and hematocrit level will also impact aggregation. Such factors may be accepted as part of the intrinsic variation across samples. With respect to the present discussion, a 3% dextran concentration will typically be suitable in a given buffer used for separation as discussed herein, though other concentrations and ranges are also described and may be useful in particular contexts and situations. As may be appreciated, increasing the dextran concentration increases red blood cell aggregate size, but also increases density, osmolality, and viscosity of the solution.

In addition to dextran solution density, as noted above, another factor in the present approach is the structural aspect related to the microfluidic channels provided within the separation device. In one implementation, at least one dimension (e.g., the height) of the microfluidic chamber or channel is scaled sufficiently small to introduce surface tension forces that act to stabilize and/or control the evolution of Rayleigh-Taylor instability. In particular, a taller microfluidic channel has lower surface tension than a thinner or narrower channel. As a consequence, Rayleigh-Taylor interface instabilities evolve more rapidly in a taller channel or chamber (e.g., 450 µm high) than a thinner channel or chamber (e.g., 225 µm high). That is, thinner channels are able to maintain the instability of having the more dense blood layered over the less dense dextran solution for longer.

During operation the Rayleigh-Taylor instability and channel height interaction (i.e., the surface tension factors) is further complicated by the ongoing red blood cell aggregation. Based on studies performed in support of the present disclosure, a taller channel (e.g., ~450 µm tall) experiences faster evolution of the Rayleigh-Taylor instability and exhibits a more rapid rise of dextran to the top portion of the device (leading to larger streams of blood sedimenting towards the bottom). In contrast, a thinner channel (e.g., ~225 µm tall) shows more balance between red blood cell aggregation and Rayleigh-Taylor instability, and has smaller blood streams at the interface. In one study, red blood cell aggregation and sedimentation was completed in ~8 min in the taller channel compared to ~15 min the thinner channel. However, 50% of the white blood cells were lost in the sedimented pellet of the taller channel (due to the larger streaming effect), compared with 20-30% in thinner channel. With this in mind, experiments suggest that the microfluidic channel height should be thinner than 450 µm in order to achieve high red blood cell depletion while maximizing white blood cell recovery. While thinner channels may increase the sedimentation time, white blood cell recovery may be enhanced due to losing fewer white blood cells in the sedimented pellet of aggregated red blood cells. Thus, there is a trade-off between white blood cell recovery and sedimentation time in terms of operational considerations.

Red Blood Cell Aggregation: Study and experimental observations—While density of the dextran solution is discussed above in a generally theoretical context, in one study the dextran solution density was adjusted to observe the relationship between density and device performance in an experimental setting. In this study the density of the dextran solution was adjusted using a low molecular weight species, such as glucose. In particular, identical devices with different dextran densities (e.g., 1.02 g/mL density versus 1.05 g/mL density) were tested and observed to show a marked difference in performance with respect to red blood cell aggregation and white blood cell recovery. Aggregated red blood cells sedimented more slowly through the denser dextran solution due to the slower evolution of the Rayleigh-Taylor instability and increased viscosity of the solution. After sedimentation was complete, a 10-15% increase in white blood cell collection was observed for the higher density dextran solution. However, the RBC: WBC ratio was roughly doubled compared to the lower density dextran (though still <20:1). It should be noted that the density adjustment was performed using a low molecular weight species (such as glucose). This minimized the likelihood of increasing the aggregability of the solution, as might be expected for a density adjustment using 500 kDa dextran. A low molecular weight species also minimized the viscosity increase associated with the density increase. This helped to ensure that the impact on the red blood cell aggregate sedimentation rate was minimized.

One further factor with respect to red blood cell aggregation and/or white blood cell recovery relates to extraction volume. In particular, it can be advantageous to minimize the volume in which the white blood cells and other blood components are extracted in order to minimize the time required to process a sample downstream. In general, a suitable extraction volume is expected to be at least as large as the input volume (e.g., 30 µL in one implementation), with the need to extract some additional volume due to some white blood cells settling over the separation time or being displaced by dextran due to the Rayleigh-Taylor instability. As shown in FIG. 1, which depicts study results for the total number of white blood cells recovered as a function of sample volume extracted from the top of the device, while absolute extraction numbers are variable (in large part due to blood sample-to-sample variability), some basic trends are clear. For example, per the depicted results, the vast majority of the white blood cells that will be recovered in a given experiment are recovered within the uppermost 100 µL. For experiments from which 100,000 cells were recoverable, this target was typically achieved within the first 50-60 µL of extract.

Figure 2:
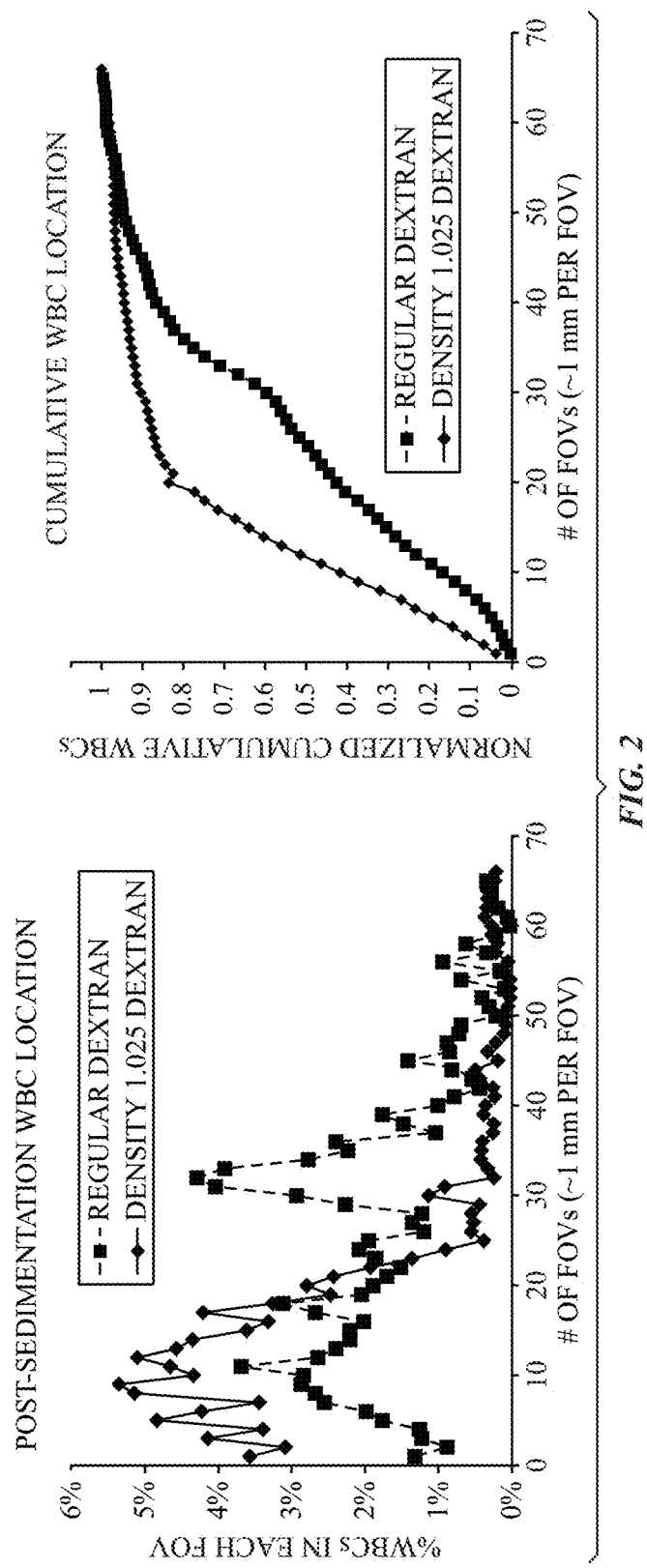
FIG. 2 depicts results of imaging a separation device used to evaluate the positions of white blood cells after separation using different density and/or osmolality dextran solutions, in accordance with aspects of the present disclosure.

These experiments related to extraction volume were performed with a 3% dextran solution (no density increase). By increasing the density of the dextran solution, it was possible to extract more white blood cells in a smaller volume. The effect of increasing the density/osmolality of the dextran solution can be more easily understood by staining the white blood cells and imaging the separation device after sedimentation has been complete. The results of this imaging are shown in FIG. 2, where the X-axis in depicts the location of the white blood cells in the separation device at the point where the separation was halted (with white blood cells still in the separation device). As shown in FIG. 2, the higher concentration of white blood cells where in the upper portion of the device when the density of dextran was increased. In particular, imaging of the device (top-to-bottom along the centerline) revealed the relative positions of white blood cells after sedimentation in devices with different dextran densities. In the higher-density dextran device, more white blood cells were located in the upper portion of the device (field-of-views (FOVs) 0-25, whereas the white blood cells were distributed over a greater range in the lower density device.

Figure 3:
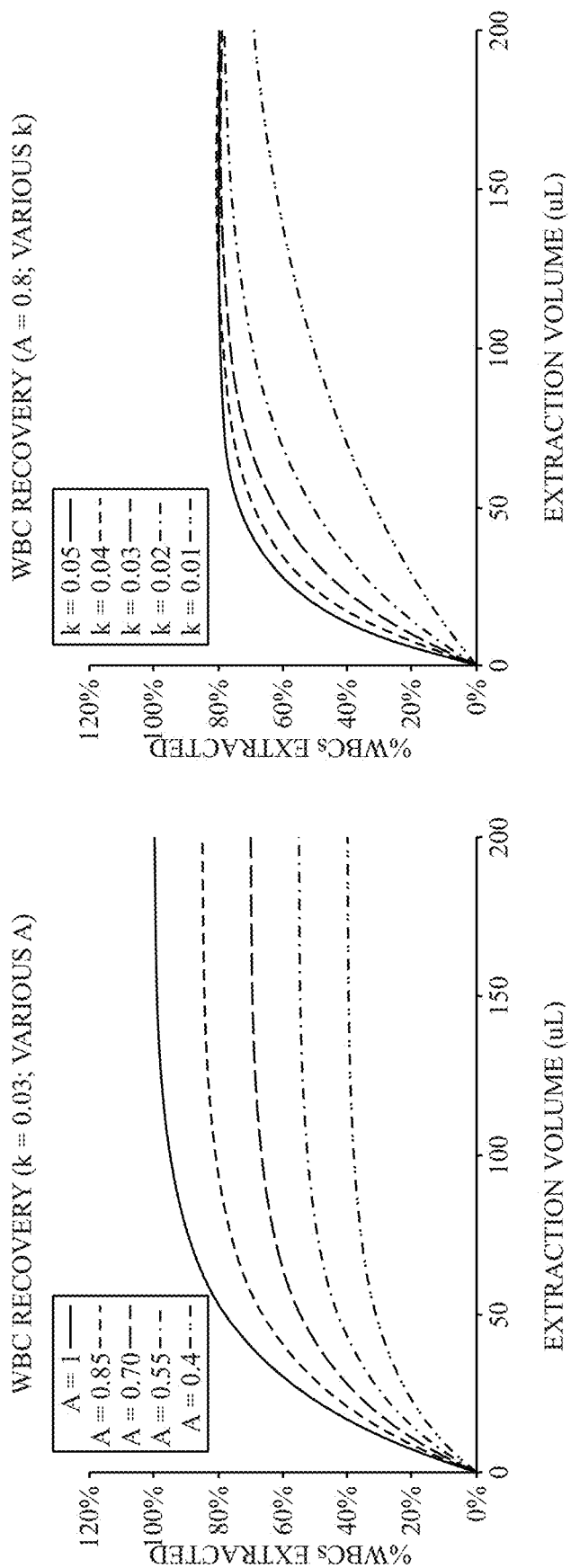
FIG. 3 depicts effects of varying A and k on white blood cell recovery, in accordance with aspects of the present disclosure.

With the aggregation and separation factors (e.g., dextran solution density and osmolality, microfluidic channel dimensions, sample size, and so forth) discussed above in mind, a number of further experiments were performed using different densities and osmolalities of dextran solution, which allowed a generalized model of the aggregation process to be estimated. The shape of the curve describing white blood cell extraction percentage (% WBC) as a function of volume, V, appeared consistent across experiments and can be estimated as an asymptotic equation of the form:

$$\% \text{ WBCs Extracted}(V) = A(1 - e^{-kV}) \qquad (1)$$

where A is the upper asymptotic limit of WBC extraction, k is a rate constant describing the volume over which that asymptote is approached, and V is the volume of the extraction. The observed effects of varying A and k are shown in FIG. 3, with the effects of varying A shown on the left and the effects of varying k shown on the right. The parameter A has a theoretical upper limit of 1 (i.e., 100% recovery).

In experiments done in support of the present disclosure, parameter A was observed to range from 0.5 to nearly 0.8 for conditions that are typical in the present red blood cell depletion device, as discussed in greater detail below. The parameter k would be expected to have a maximum around 0.1 for 30 µL blood input, extracting 100% of recoverable white blood cells in 30 µL of extract. In practice, sedimentation of the white blood cells occurs along with the red blood cell aggregates, so k<0.1 is expected. Observed values of k typically ranged from 0.02-0.05, depending on the experimental conditions.

Figure 4:
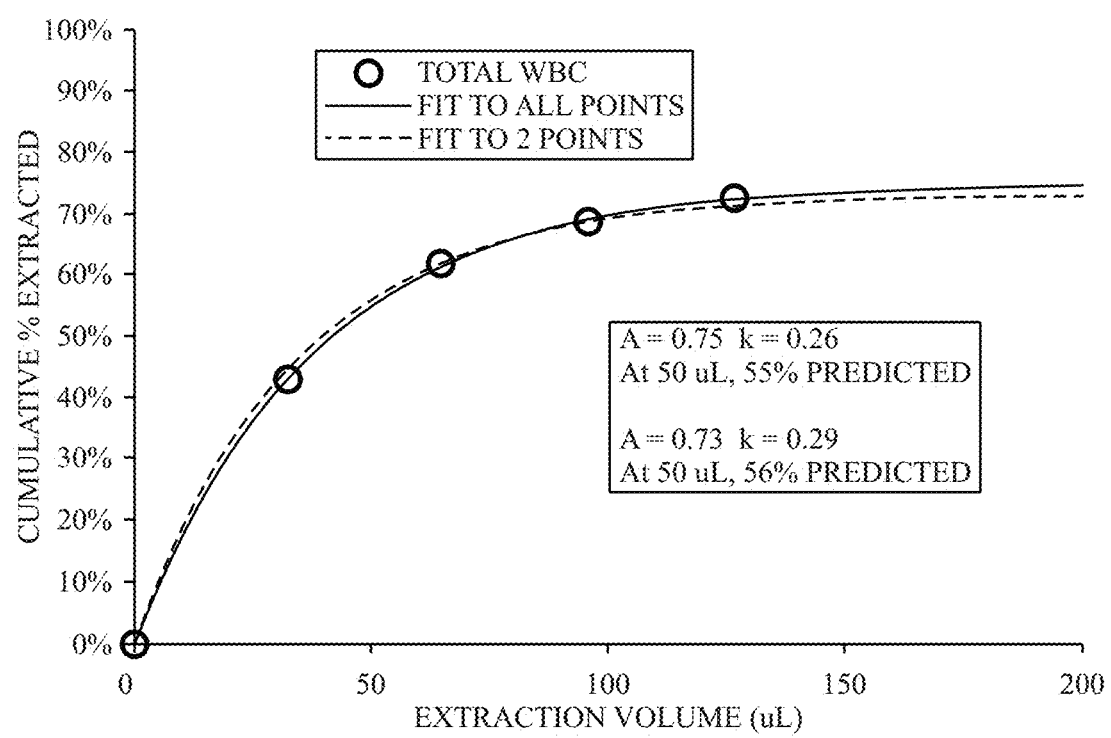
FIG. 4 depicts a white blood cell extraction curve, in accordance with aspects of the present disclosure.

For the expected range of A and k values for normal operating conditions of the present separation device, a white blood cell extraction curve (FIG. 4) could be estimated with two data points of around 50 µL and 100 µL extraction volume aliquots along with the origin (i.e., zero point). In particular, the estimated curve using these three points was found to be nearly identical to the curve estimated using more (e.g., four or five) data points. The extraction model and two-point fit create a standardized experimental process and a simple numerical mechanism of comparing outcomes at different experimental conditions.

Based on the extraction model, the effects of density and osmolality on white blood cell extraction can be understood more clearly: The density of the dextran-based aggregation medium primarily affects parameter k (determines extraction volume), while the osmolality of the medium primarily affects parameter A (determines ultimate extraction efficiency). Experiments show that both have an impact on sedimentation time (increased density increases sedimentation time, while increased osmolality reduces it).

Figure 5:
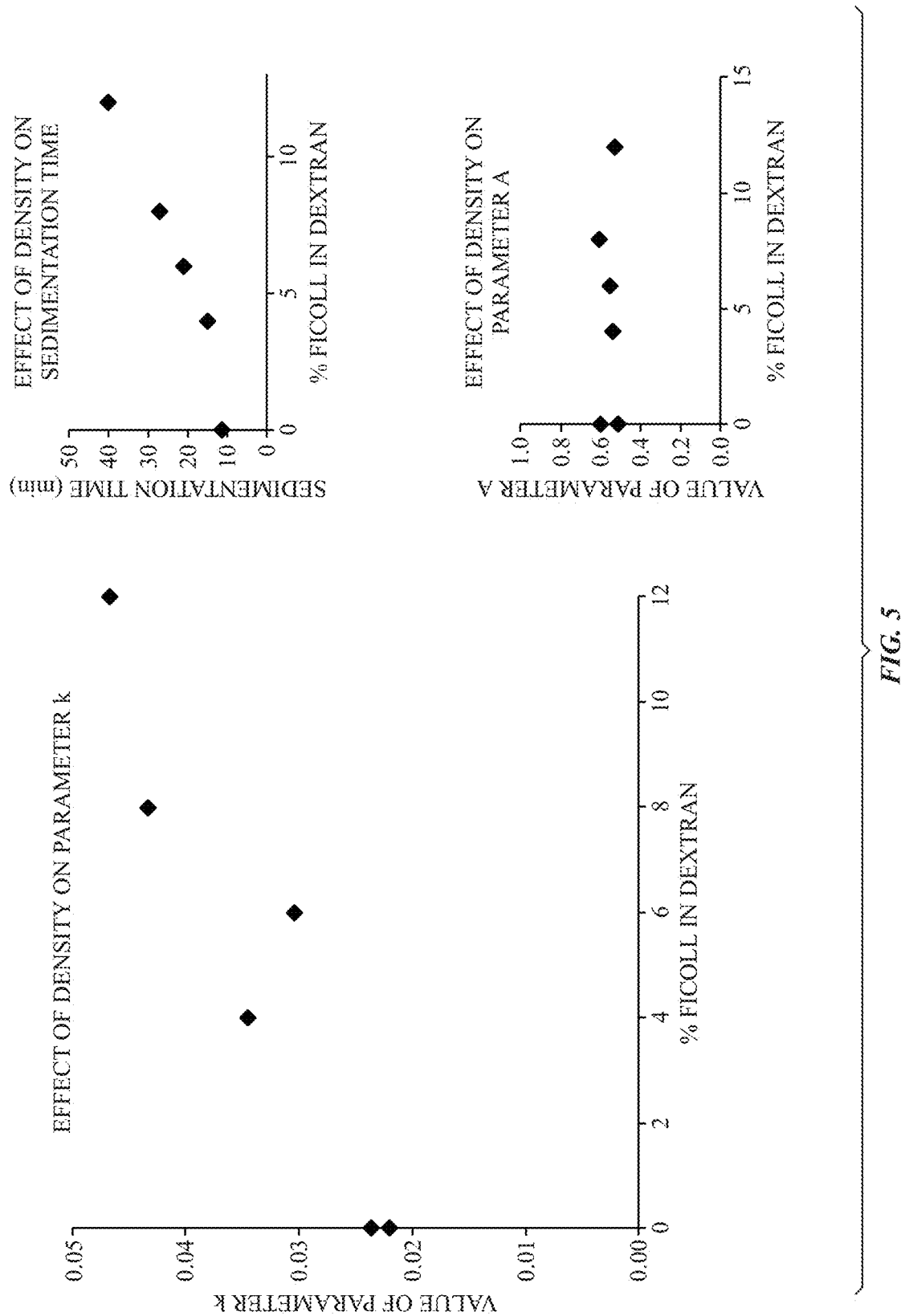
FIG. 5 depicts the effects of adjusting dextran solution density, in accordance with aspects of the present disclosure.

The effects of adjusting dextran solution density are shown in FIG. 5, which shows effects of density on parameter k (left), sedimentation time (upper right), and parameter A (lower right) at fixed (physiologic, approximately 290 mOsm/kg) osmolality, where increasing percentage of Ficoll increases the density of the solution. Note the clear impact of density on parameter k and lack of impact on parameter A. In particular, as shown in FIG. 5, the rate of increase in parameter k with increased density starts to taper off at around 6% added sugars, while the sedimentation time continues to rise. In view of this observation, in certain implementations of a device as discussed herein the separation medium should have around 6% added sugars to increase the density and maximize parameter k while limiting the sedimentation time increase.

Figure 6:
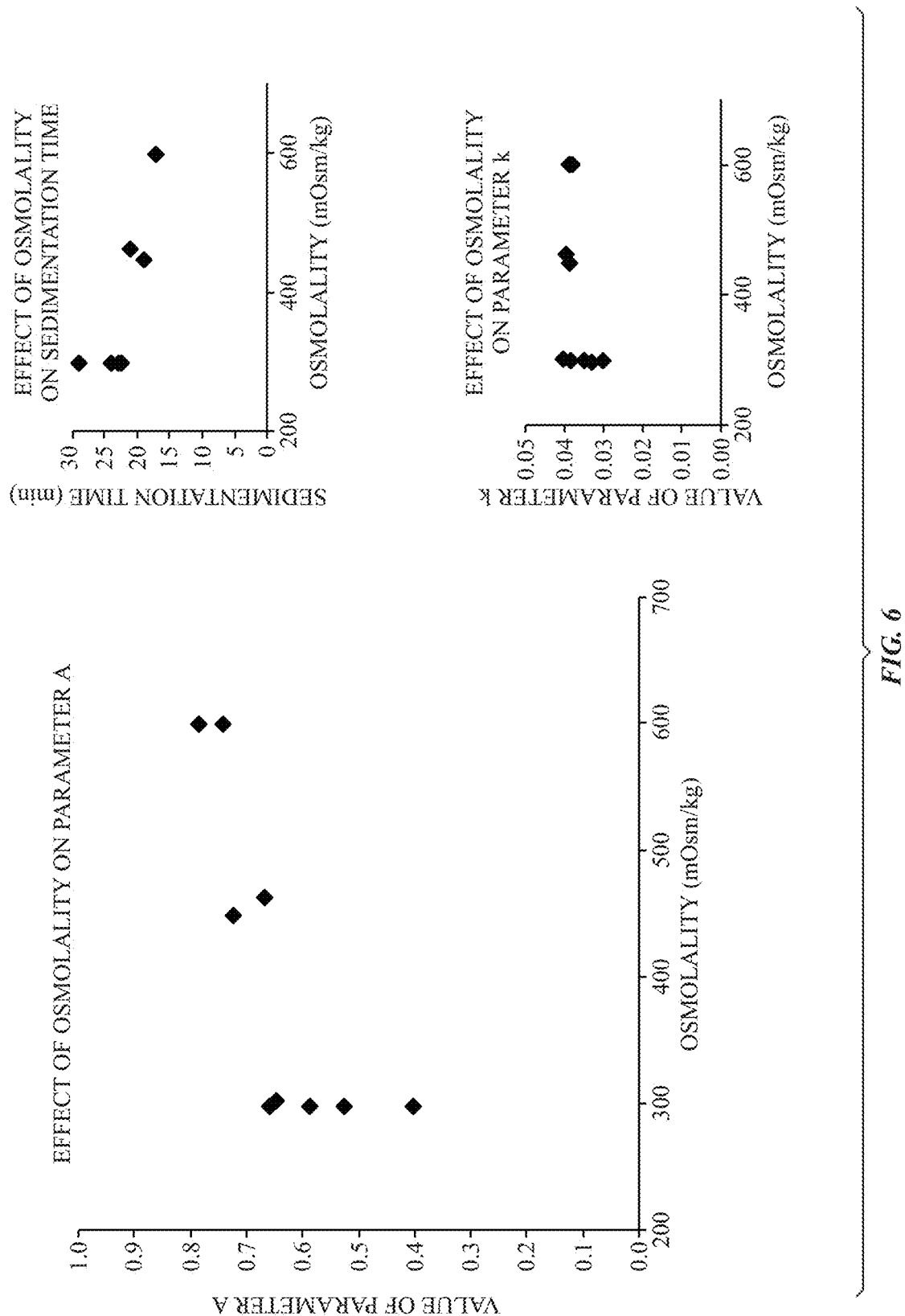
FIG. 6 depicts the effects of adjusting dextran solution osmolality, in accordance with aspects of the present disclosure.

The effects of adjusting osmolality of the solution are shown in FIG. 6, which shows effects of osmolality on parameter A (left), sedimentation time (upper right), and parameter k (lower right) at 6% sugars added to the dextran solution to increase density. Varied proportions of Ficoll-70 (minimally affects osmolality) and glucose (significantly increases osmolality) were used to make up the added 6% sugars. Note the impact of osmolality on parameter A and relative lack of impact on parameter k. In particular, as shown in FIG. 6, an increased osmolality may be useful in certain implementations. While a 600 mOsm/kg dextran solution may be too great an osmolality increase for the cells in some instances, a lower increase (e.g., 400 mOsm/kg) might be acceptable. If an osmolality increase is detrimental to the downstream assay, acceptable white blood cell extraction can still be obtained under physiological osmolality conditions with a small increase in sample input volume.

Figure 7:
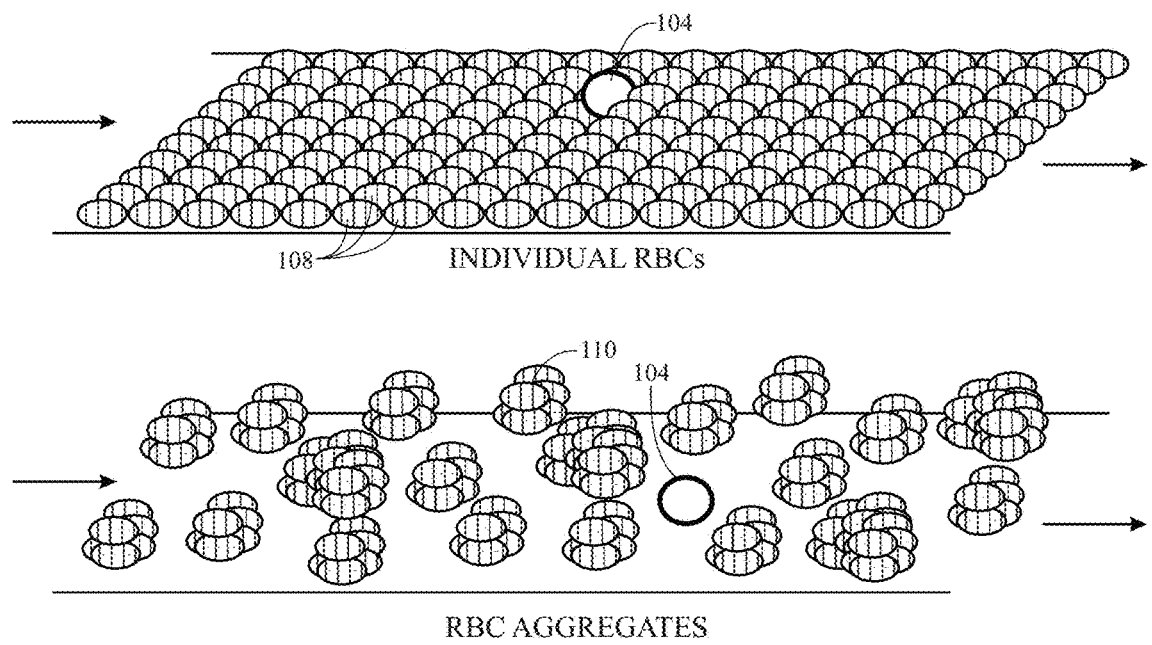
FIG. 7 depicts white blood cell spatial relations in the context of unaggregated and aggregated red blood cells, in accordance with aspects of the present disclosure.

White Blood Cell Isolation: Principles of Operation—The efficiency of capturing white blood cells on a surface over which whole blood is flowed is typically quite low due to the overwhelming number of red blood cells that block potential binding spots. In particular, red blood cells outnumber white blood cells in whole blood by ~1000:1. By first aggregating and partially separating the red blood cells, as discussed above, high efficiency white blood cell capture can be realized since the red blood cell aggregates open up space for white blood cells to bind. A generalized view of this concept is shown in FIG. 7, where white blood cells 104 are shown in the context of both unaggregated red blood cells 108 (top) and aggregated red blood cells 110 (bottom). Furthermore, since the majority of red blood cell aggregates 110 flow through the device first (due to prior partial separation in the red blood cell aggregation device or device segment), the majority of white blood cells that flow in after the red blood cells have very little binding competition. That is, the relative number or concentration of white blood cells relative to potential binding cites is increased in view of the red blood cell aggregation performed prior to exposure of the white blood cells to the binding sites.

Therefore, in accordance with the present approach, a sample from which the red blood cells have been aggregated can be processed to collect (i.e., isolate and purify) the remaining white blood cells. In one implementation, a microfluidic device as discussed herein receives the output of the red blood cell aggregation device or device segment (in an integrated implementation) and immobilizes the white blood cells with minimal capture of red blood cells, red blood cells aggregates, or other blood components, which may flow through the device. Though white blood cell capture is discussed generally herein by way of example, it should be appreciated that the sample from which red blood cells have been separated or aggregated out may be processed instead of or in addition to so as to capture one or more of plasma proteins, lipids, circulating nucleic acids, circulating tumor cells, viruses, or bacteria which may be of interest.

Integration of the red blood cell aggregation and white blood cell capture devices or segments (of an integrated device) maximizes the white blood cell capture efficiency by allowing the entire blood/dextran mixture, after red blood cell aggregation, to be flowed through the white blood cell capture device. This minimizes the chance of losing white blood cells that might sediment along with the aggregated red blood cells. In certain implementations discussed herein, integration may be by connecting an output of a red blood cell aggregation component to an input of a white blood cell capture component, so that there is continuity of flow between the components. Alternatively, in other implementations, the white blood cell capture components e.g., an affinity surface, such as an antibody coated wall, may be provided as a wall or surface of the red blood cell aggregation component, so that these functions are performed in the same vessel.

Once the white blood cells are immobilized, either in the aggregation component or a separate collection component, live cell assays may be conducted (applying stimuli, real-time monitoring of cellular activity, and so forth), and/or the biochemical state could be frozen (by fixing the cells) to allow for analysis of the white blood cells at a specific point in time. Furthermore, the white blood cells can be released from the surface and flowed out of the capture device for further analysis. Further, different white blood cell subtypes can be captured by selecting the appropriate capture antibody, such as an antibody specific for proteins on the white blood cell type(s) of interest. Using such selective capture approaches, white blood cell subtypes can be segregated spatially on the surface by immobilizing different antibodies at different locations along the capture channel.

Figure 8:
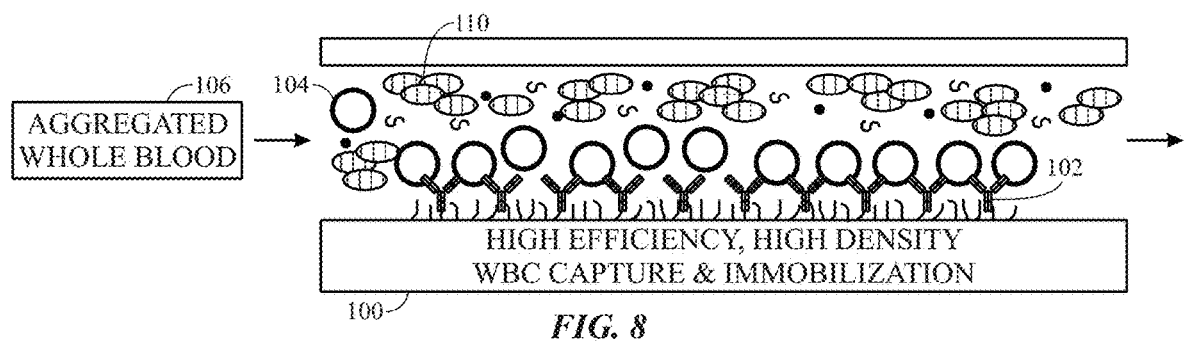
FIG. 8 depicts a conceptualized view of white blood cell binding, in accordance with aspects of the present disclosure.

With the preceding in mind, an example of a white blood cell capture approach is shown in FIG. 8, in which a device surface 100 is coated with antibodies 102 having an affinity for white blood cells 104. By way of example, in one such approach the white blood cells may be immobilized via affinity capture using a surface coated with anti-CD45 antibody. As whole blood 106 containing aggregated red blood cells 110 (e.g., an output from a red blood cell aggregation device or segment as discussed above) is passed over the surface 100, white blood cells 104 are bound by the antibodies 102, while aggregated red blood cells 110 and other blood components pass through. As noted above, the surface 100 may be a surface of the red blood cell aggregation device or of a separate white blood cell collection device in fluid communication with the red blood cell aggregation device.

Figure 9:
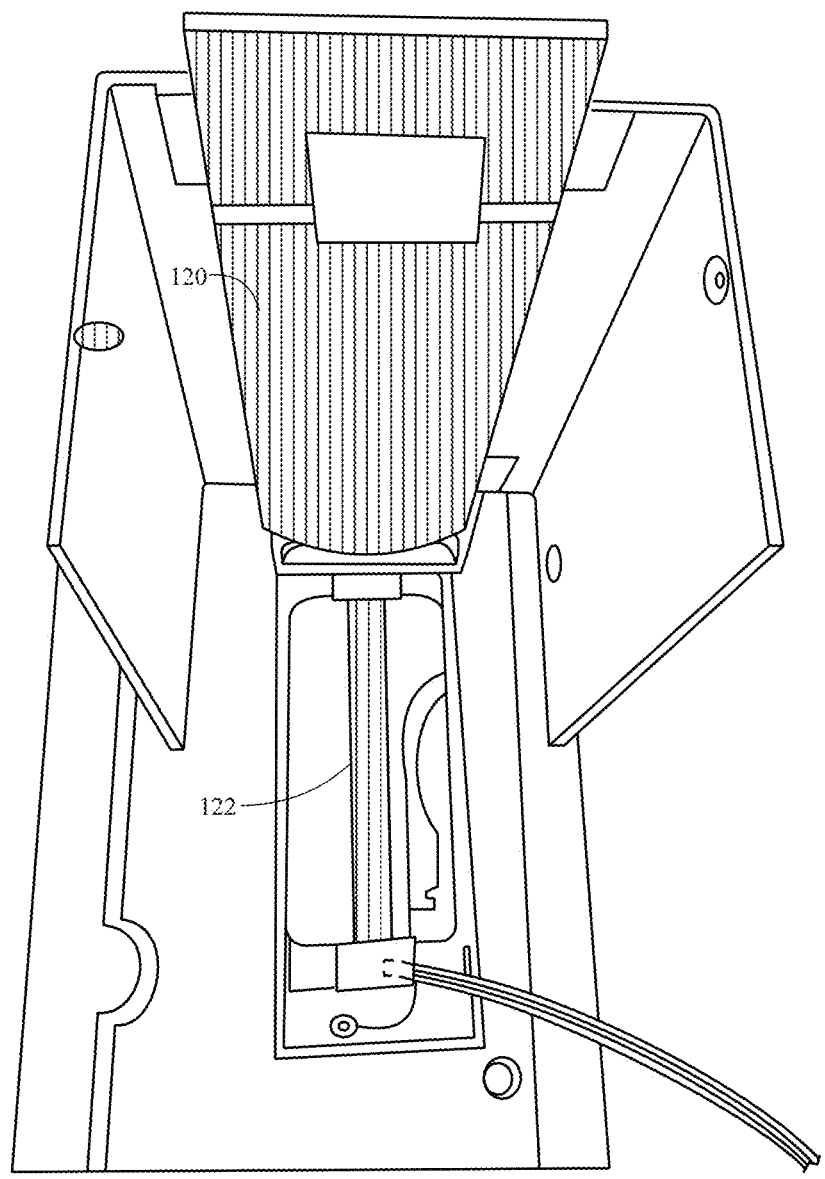
FIG. 9 depicts a red blood cell aggregation and white blood cell capture components of a device, in accordance with aspects of the present disclosure.
Figure 10:
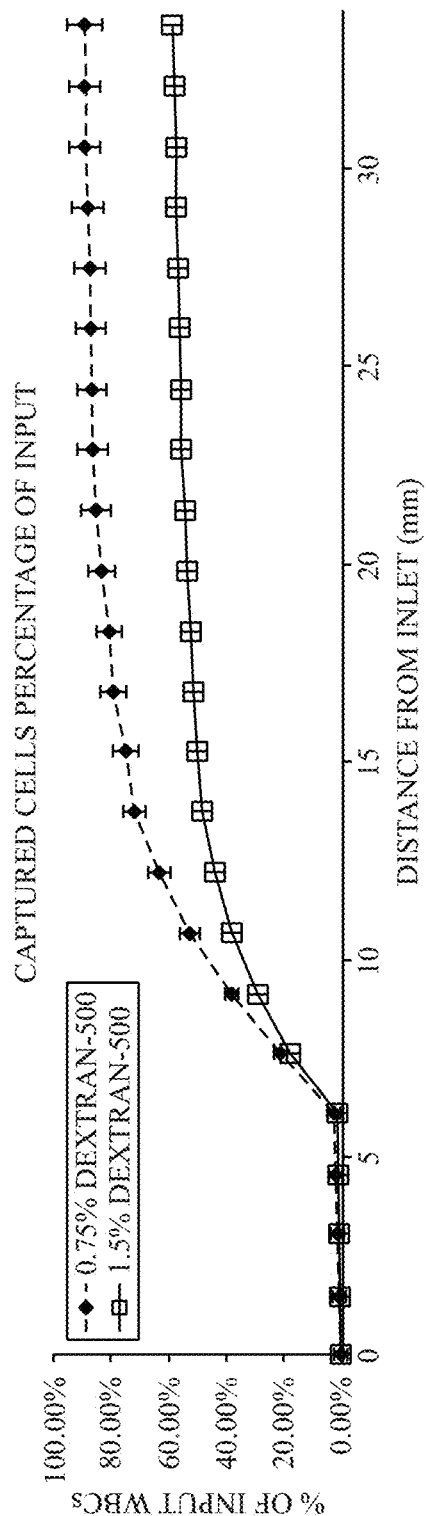
FIG. 10 depicts effects on captured cell percentage as a function of density of the red blood cell aggregation media, in accordance with aspects of the present disclosure.

White Blood Cell Isolation: Study and experimental observations—As shown in FIGS. 9 and 10, experiments involving a direct connection between the red blood cell aggregation and white blood cell capture devices exhibited white blood cell recovery of greater than 80%. In particular, FIG. 9 depicts an example of a red blood cell aggregation device or segment 120 (working in accordance with the preceding discussion) whose output feeds directly into a white blood cell capture device or segment 122. This direct integration minimizes cell losses that would typically be significant if transferring fluids between the modules using macro-scale methods. As noted above, however, in alternative implementations the white blood cell capture surface may be provided in the red blood cell aggregation segment as well. Experimental data also indicates that the relative capture of white blood cell subtypes is comparable to the percentages in whole blood. As shown in FIG. 10, in these examples, reducing the density of the red blood cell aggregation media (0.75% dextran-500 instead of 3%) improved the white blood cell recovery to greater than 80%. The white blood cells sediment faster in the lower density 0.75% dextran solution, enabling improved capture and reduced workflow time.

Figure 11:
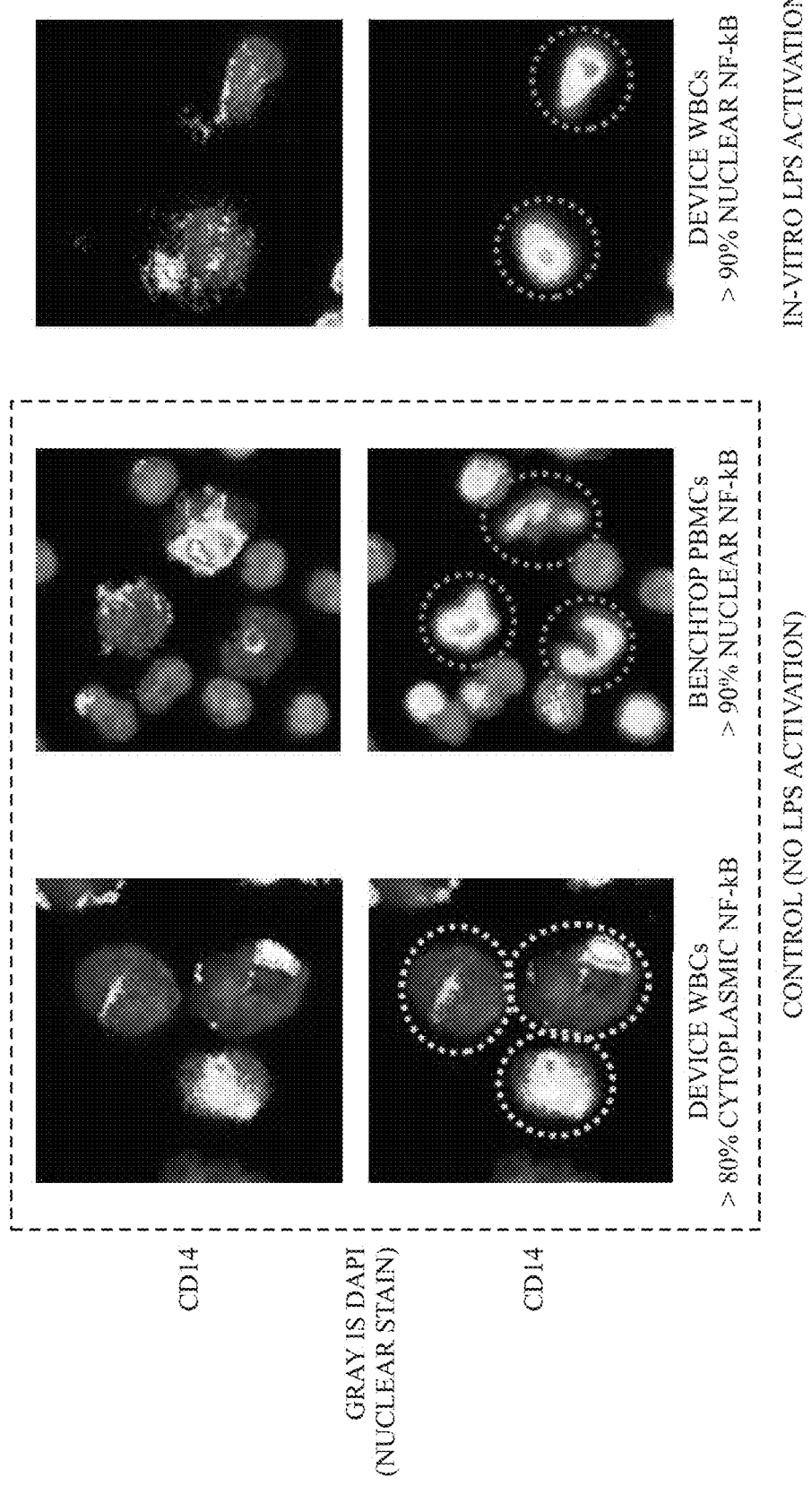
FIG. 11 depicts a comparison between the NF-κB localization of white blood cells prepared with a conventional method and white blood cells prepared with an integrated microfluidic device in accordance with aspects of the present disclosure.

Based on studies performed based on the present approaches, it has been demonstrated that the integrated blood sample preparation workflow described herein is gentle on the white blood cells and does not appear to cause biochemical activation. By way of example, FIG. 11 shows a comparison between the NF-κB localization of white blood cells prepared with a conventional method (i.e., centrifugation with Ficoll-Paque density-gradient media), and white blood cells prepared with an integrated microfluidic device, as discussed herein. As seen in these results, this biomarker is clearly activated in the Ficoll-Paque centrifugation case, and not activated in the case of the microfluidic device.

In particular, circled cells in the images are the CD14+ monocytes (left column) Monocytes prepared by the integrated fluidic device described herein show a high percentage of overlap between membrane-bound CD14 and NF-κB, which indicates that the NF-κB is localized in the cytoplasm (middle column). In contrast, monocytes prepared by Ficoll-Paque centrifugation consistently exhibit nuclear NF-κB where there is minimal overlap with CD14 (right column) Monocytes prepared by the integrated fluidic modules and then activated with lipopolysaccharide (LPS) exhibit the anticipated nuclear NF-κB, confirming LPS activation. All images were acquired at 20× magnification.

Sample Integrated Red Blood Cell Aggregation and White Blood Cell Capture Device—With the preceding in mind, a white blood cell capture device may combine the red blood cell aggregation and white blood cell capture channels into a fluidic cartridge 200 (FIG. 12) that houses reagents for subsequent analysis of the purified and immobilized white blood cells. In one such example, the microfluidic chip or cartridge 200 integrates microvalves 214 for reagent switching. This design allows for complete automation of the process from whole blood loading through white blood cell capture and analysis.

Figure 12:
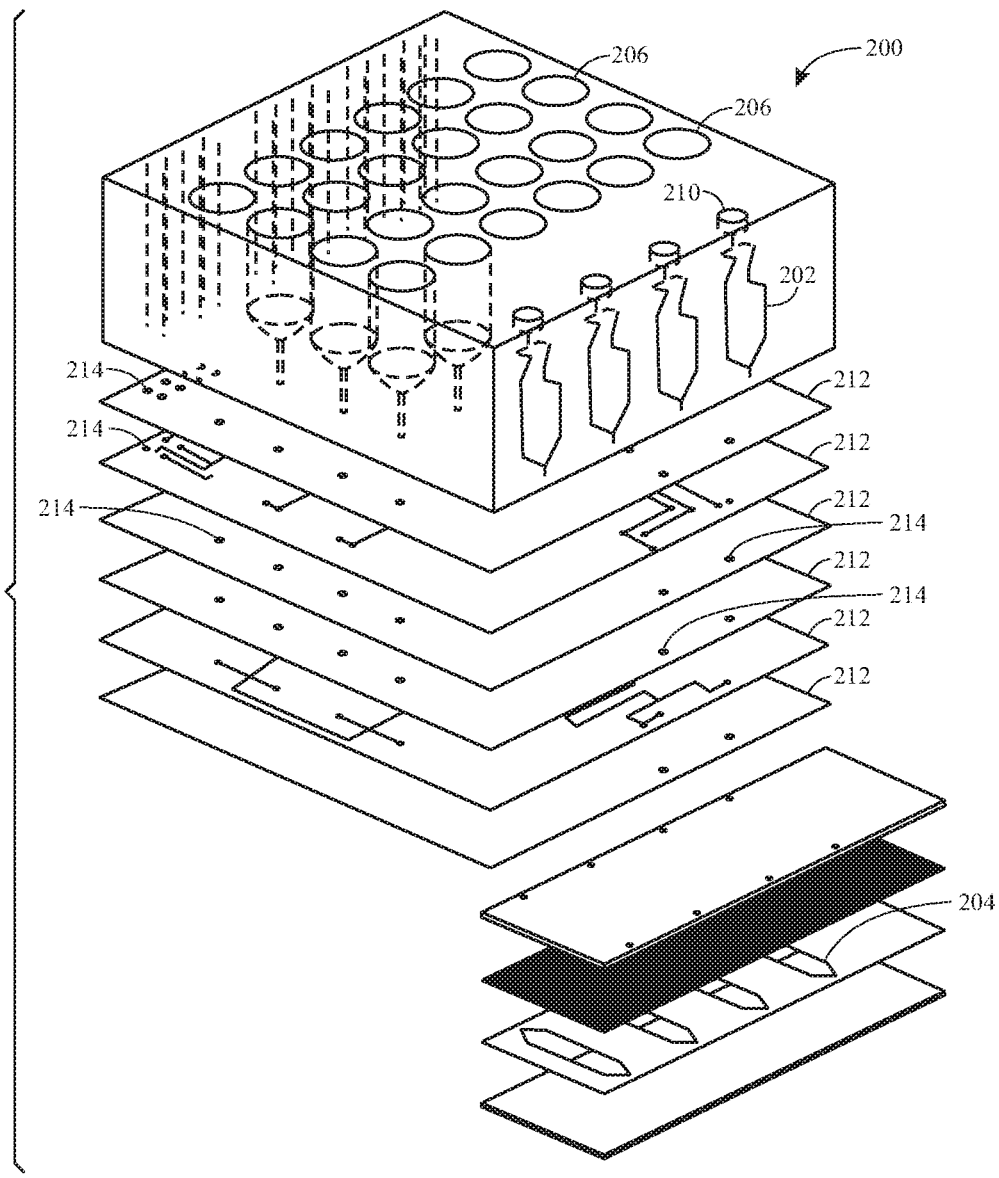
FIG. 12 schematically depicts a white blood cell capture device embodied as a fluidic cartridge or chip, in accordance with aspects of the present disclosure.

FIG. 12 depicts a design rendering of one such cartridge 200 showing the various layers 212 of the fluidic cartridge that integrates the red blood cell aggregation channels 202, white blood cell capture channels 204, and reagents (reagent wells 206) for analysis of the captured white blood cells. In one implementation, the red blood cell aggregation channels 202 are approximately 5 mm across and 0.225 mm in height. In the depicted example, whole blood may be loaded in to the blood sample loading wells 210 for processing as discussed herein. Blood loaded into wells 210 may or may not be treated with an anticoagulant prior to loading. Four parallel capture modules are shown in FIG. 12, but more (e.g., 6) could fit on a capture slide. As noted above, instead of providing separate white blood cell capture channels 204, the red blood cell aggregation channels 202 may instead be fabricated so as to include one or more affinity surfaces (e.g., antibody coated surfaces) specific to white blood cells or the blood component(s) of interest so that red blood cell aggregation and blood component capture occur in the same chamber.

With the preceding discussion mind, and by way of summary, technical effects of the invention include a device and/or methodology in accordance with the present approach consists of one or both of: (1) a mechanism of separating erythrocytes from other constituents of blood, and (2) a mechanism of purifying leukocytes from blood by flowing the output of the first aspect over an affinity capture surface. The first ('separation') portion assists in separating erythrocytes (red blood cells) from other cells in blood, such as by aggregation of the red blood cells. A suitable aggregation device or device component uses chambers with at least one small dimension (e.g., a microfluidic chip) to control the interaction of the blood with a solution containing a high molecular weight polymer (e.g., dextran) to achieve separation. The process is effectively hands-free. This is in contrast to mixing blood with the polymer solution. This approach is unique in that it provides efficient separation of erythrocytes from small volumes of blood (such as might be used in a field test) with a low dilution of the sample.

In one implementation, the separation component works by controlling the process of red blood cell aggregation in the presence of dextran. Whole blood is introduced to the dextran solution in a controlled manner within a microfluidic channel. After loading the sample, the blood and dextran begin to slowly mix at the interface. As red blood cells aggregate due to the dextran, the red blood cell aggregates sediment under gravity and move into the dextran solution towards the bottom of the device (leaving the vast majority of white blood cells behind). The red blood cell depletion efficiency is a function of the interplay between surface tension (controlled by channel geometry), instability of the blood/dextran interface (Rayleigh-Taylor instability), and the dextran aggregation properties (e.g., dextran concentration and molecular weight, as well as solution density, temperature, osmolality, and so forth). The use of a microfluidic device allows surface tension to be controlled and used to achieve a degree of stability in an otherwise unstable interface, allowing for a no-mixing approach which in turn enables gravity-based separation of the erythrocytes away from the location of the leukocytes. This is in contrast to a mixing approach, where the blood starts out uniformly distributed and simply partitions itself within that same volume. In particular, the present approaches use surface tension, in the context of microfluidic devices, to allow the blood to be layered over a less-dense separation medium.

The second ('capture') portion, if provided as a separate segment or component, flows the output of the separation (i.e., aggregation) device over an affinity capture surface to isolate a high-purity sample of leukocytes. Alternatively, as noted above, the affinity capture surface may be provided in the same chamber as aggregation occurs in. An example of a suitable capture antibody is CD45 (pan-leukocyte), however there are a wide variety of antibodies or other linking agents (e.g., DNA) that could be used (singly or jointly) to capture any of the leukocyte subtypes, CTCs, platelets, bacteria, free DNA, etc. The erythrocyte sequestration (both by aggregation and by physical separation via sedimentation) enables higher capture efficiency than would be expected from whole or diluted blood. These devices may be highly automated, relatively fast, able to operate with very low blood volumes, and appear to induce minimal activation of the leukocytes.

The capture aspect works by optimizing delivery of a separated sample to an affinity surface. This minimizes physical competition for binding sites. The separation stage aggregates the erythrocytes, and gravity pulls them to the bottom of the separation device. After a set time, the contents of the separation device begin to flow out the bottom of the device and into the capture device or out for disposal (if the capture surface is integrated with the aggregation chamber). The aggregated erythrocytes pass over the affinity surface first. The erythrocytes do not bind to the affinity surface (enabling high purity leukocyte capture). As discussed above, the aggregated erythrocytes take up less surface area than non-aggregated erythrocytes, improving the chances for any accompanying trapped leukocytes to bind to the surface (recovery). After the erythrocytes pass through, many of the leukocytes (from the top or supernatant portion of the separation stage) will follow. Without erythrocytes, these leukocytes interact freely with the affinity surface, providing for a very high efficiency leukocyte capture.

This approach is a simple, highly-automatable approach for separating leukocytes from erythrocytes, even from very small (e.g., 30 µl) volumes of blood. The approach does not require laboratory equipment (such as a centrifuge) or trained personnel. The removal of erythrocytes from leukocytes is necessary for many leukocyte-specific assays, as the erythrocytes outnumber leukocytes by ~1000:1, creating significant issues with binding kinetics or background noise. Multiple separation devices as described herein could be parallelized to deal with higher blood volumes. Cells are minimally activated, allowing for high fidelity downstream use. The addition of the capture stage provides a highly automated mechanism of turning a small volume of whole blood into a minimally-activated, surface-bound, customizable leukocyte population in under 2 hours with low cell losses. Further manipulation (live cell assays) and preparation steps (fixation, FISH, immunocytochemical staining, etc.) are readily automated for this sort of sample. Such samples (bound or unbound) could be useful for a wide variety of applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A multi-layer microfluidic device, comprising:
   one or more loading wells accessible on a first surface of the multi-layer microfluidic device, wherein each of the one or more loading wells comprises a loading well outlet;
   a longitudinal axis along a direction from a first layer of the multi-layer microfluidic device to a second layer of the multi-layer microfluidic device;
   vertical aggregation channels, wherein each vertical aggregation channel comprises an aggregation channel inlet and an aggregation channel outlet, wherein each vertical aggregation channel is in continuous fluid communication with a respective loading well of the one or more loading wells via the aggregation channel inlet of the vertical aggregation channel coupled to the loading well outlet of the respective loading well at a first longitudinal position along the longitudinal axis;
   at least one separate, respective output channel comprising an output channel inlet and an output channel outlet, wherein each aggregation channel of the aggregation channels is in continuous fluid communication with the at least one separate, respective output channel via the aggregation channel outlet of the vertical aggregation channels coupled to the output channel inlet of the output channel at a second longitudinal position along the longitudinal axis, wherein the second longitudinal position is downstream of the first longitudinal position relative to the longitudinal axis, wherein an inner diameter of each aggregation channel tapers towards the second longitudinal position, wherein each diameter of the output channel is substantially perpendicular to the longitudinal axis, wherein at least one diameter of the output channel is less than or equal to 450 µm, and wherein the aggregation channels are disposed on the first layer of the multi-layer microfluidic device;
   at least one capture channel comprising a capture channel inlet, wherein the at least one capture channel is configured to receive an output fluid from the output channel of one or more of the aggregation channels when in use via the output channel outlet of the output channel and the capture channel inlet of the capture channel at a third longitudinal position along the longitudinal axis, wherein the third longitudinal position is downstream of the second longitudinal position relative to the longitudinal axis, and comprising an antibody coated surface configured to selectively bind at least one type of blood cell in the output fluid, wherein the at least one capture channel is downstream of the aggregation channels in the multi-layer microfluidic device, wherein a longest dimension of the at least one capture channel is substantially perpendicular to the longitudinal axis and is crosswise to a longest dimension of the aggregation channel that is substantially parallel to the longitudinal axis, wherein the at least one capture channel is disposed on the second layer of the multi-layer microfluidic device;
   one or more reagent wells disposed adjacent to the one or more loading wells and having an opening at the first surface of the multi-layered microfluidic device, wherein the one or more reagent wells is fluidly coupled to the at least one capture channel and configured to hold reagents for treating or analyzing cells captured by the at least one capture channel; and
   a valve positioned between the at least one capture channel and the one or more aggregation channels.

2. The multi-layer microfluidic device of claim 1, further comprising: one or more microvalves.

3. The multi-layer microfluidic device of claim 1, wherein the valve comprises a microvalve.

4. The multi-layer microfluidic device of claim 1, wherein each aggregation channel of the aggregation channels has at least one dimension perpendicular to the longitudinal axis that is less than or equal to 225 µm.

5. The multi-layer microfluidic device of claim 1, wherein the respective aggregation channels are proportioned so as to generate a surface tension between a blood sample and a solution of a high-molecular weight polysaccharide, when present, sufficient to stabilize the blood sample over the solution within the aggregation channels, wherein the blood sample is higher density than the solution.

6. The multi-layer microfluidic device of claim 1, wherein the diameter of the output channel of each aggregation channel of the aggregation channels that is less than or equal to 450 µm is perpendicular to the longitudinal axis.

7. The multi-layer microfluidic device of claim 1, wherein a dimension of the aggregation channels is variable along the longest dimension that is substantially parallel to the longitudinal axis.

8. The multi-layer microfluidic device of claim 1, wherein the one or more loading wells comprise an inlet opening on the first surface, and wherein the inlet opening is smaller than the opening of the one or more reagent wells.

* * * * *